United States Patent [19]
Suson et al.

[11] Patent Number: 5,830,233
[45] Date of Patent: Nov. 3, 1998

[54] METHODS AND DEVICES FOR PERFORMING A TEMPORARY TARSORRHAPHY

[75] Inventors: John Suson, 4445 Danbury Dr., Brookfield, Wis. 53045; Williford Smith, Milwaukee, Wis.

[73] Assignee: John Suson, Brookfield, Wis.

[21] Appl. No.: 729,854

[22] Filed: Oct. 15, 1996

[51] Int. Cl.⁶ .................................................. A61B 17/04
[52] U.S. Cl. .......................................... 606/215; 128/898
[58] Field of Search .................................. 606/215, 216; 128/898

[56] References Cited

U.S. PATENT DOCUMENTS

| | | | |
|---|---|---|---|
| 3,103,218 | 9/1963 | Ajemian | 606/216 |
| 4,134,401 | 1/1979 | Galician . | |
| 4,696,301 | 9/1987 | Barabe | 606/216 |
| 5,144,944 | 9/1992 | Rice . | |
| 5,214,093 | 5/1993 | Nell et al. . | |
| 5,263,973 | 11/1993 | Cook | 606/216 |
| 5,290,292 | 3/1994 | Householder . | |
| 5,542,437 | 8/1996 | Blackmore et al. | 128/898 |

OTHER PUBLICATIONS

Sidney A. Fox, *Ophthalmic Plastic Surgery*, 4th Ed., pp. 73–85, 1970.

*Primary Examiner*—Gary Jackson
*Attorney, Agent, or Firm*—Foley & Lardner

[57] ABSTRACT

Devices and methods for performing a temporary tarsorrhaphy are provided. One device comprises two clips mounted in parallel on the upper and lower eyelids of an eye. The clips are then fastened together in a reversible manner to complete the temporary tarsorrhaphy. Each clip comprises a tube which is partially implanted in a linear fashion under the eyelid such that the tube is at a subcutaneous center portion and each end of the tube projects from the eyelid. The end portions of the tube that lie outside of the eyelid are joined together by a connecting means having first and second ends. The procedure is repeated on the lower eyelid. The connecting means are then joined together with one or more removable fasteners to complete the temporary tarsorrhaphy.

20 Claims, 6 Drawing Sheets

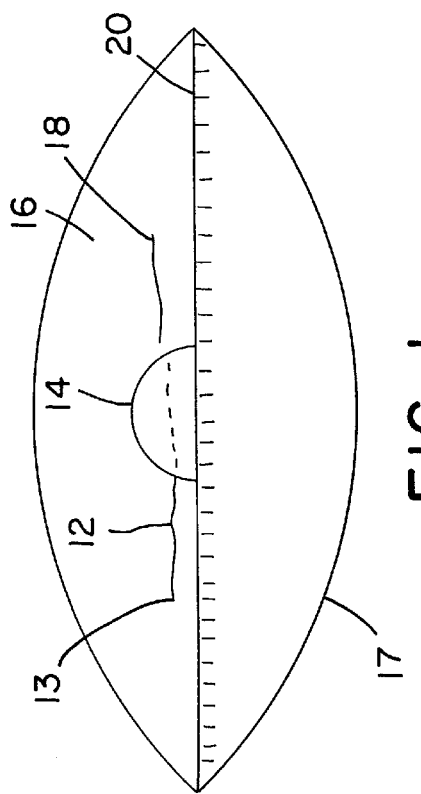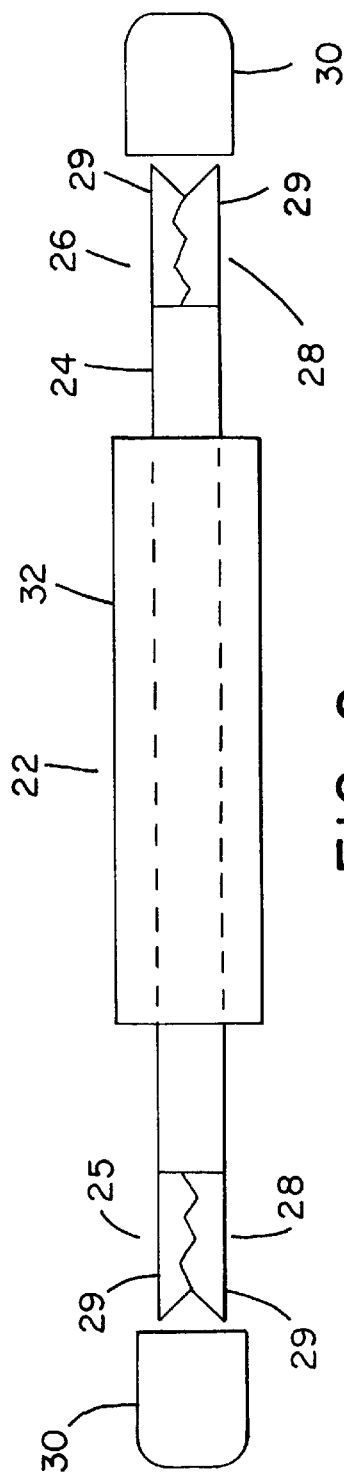

METHODS AND DEVICES FOR PERFORMING A TEMPORARY TARSORRHAPHY

TECHNICAL FIELD

The present invention relates generally to medical technology and to methods and devices for performing a temporary tarsorrhaphy.

BACKGROUND OF THE INVENTION

Tarsorrhaphy is a common ophthalmic procedure performed on damaged eyes involving surgical fusion of the upper and lower eyelid margins. The procedure has the effect of partially or fully narrowing the palpebral fissure, thereby reducing exposure of the damaged eye to the external environment, allowing the damaged eye to heal. This procedure is performed most commonly to protect an injured cornea. Examples of conditions which often call for a tarsorrhaphy include keratitis associated with severe dry eyes, non-healing corneal abrasions or ulcers due to any cause, and corneas which are in poor condition immediately following surgical procedures such as corneal transplant, vitrectomy, or glaucoma surgery with the use of antimetabolites, which in themselves are often injurious to the cornea.

The tarsorrhaphy may be one of two varieties. A permanent tarsorrhaphy may be formed wherein the eyelid margins are sealed indefinitely. More common is a procedure known as a temporary tarsorrhaphy wherein the eyelids are fastened together for a time period ranging from six weeks to several months.

Although several techniques exist for performing a temporary tarsorrhaphy, this fundamental procedure implies a surgery that is usually carried out by sewing the top and bottom eyelids together, using a fine suture. The simplest method of creating a tarsorrhaphy is to mark off the opposing areas of the upper and lower eyelids to be fused by means of scratch marks. The eyelids are then sutured together at the marks.

Several problems have been associated with temporary tarsorrhaphies. The sutures used to create the tarsorrhaphy may loosen or pull out before their function is fully accomplished. This may occur in lids whose vitality has been lowered by severe trauma or frequent surgical procedure. This also occurs in lids narrowed congenitally or by loss of tissue due to trauma. Various other techniques have been used in performing a temporary tarsorrhaphy to try to prevent the integrity of the sutures used in performing a tarsorrhaphy from being negatively impacted.

A complex tarsorrhaphy technique has been designed in which a tongue and groove are created in the lower and upper eyelids, respectively, and the tongue is then drawn up to fill the groove in the upper lid and sewn into place. However, in addition to the usual surgical problems associated with sewn-in-place tarsorrhaphies, this method requires more surgery, additional tissue disruption, and may require a longer healing time.

Other techniques also exist for performing a temporary tarsorrhaphy. Small rectangular pieces of material, known as "pegs", may be placed opposite each other on the upper and lower eyelids. The pegs are sewn to the eyelids and then to each other to accomplish the temporary tarsorrhaphy. Although this procedure is of some help in preventing loosening or tearing of the sutures, none of the temporary tarsorrhaphy methods to date have addressed the additional problem of being able to allow the eyelids to be separated in order to visualize the cornea or other parts of the eye without removing the temporary tarsorrhaphy itself.

Although it is possible to sew only a portion of the eyelids together in performing a temporary tarsorrhaphy, this allows only partial protection of the eye and allows only a portion of the eye to be inspected by the ophthalmic practitioner without removing the tarsorrhaphy. Since the purpose of the temporary tarsorrhaphy is to protect the eye and/or to promote healing, it would be advantageous to be able to easily open and reclose the eyelids at will to assess the status of the eye.

Temporary tarsorrhaphies are intended to last for a period of time ranging from six weeks to several months. However, it has been found that by using any of the known methods for a temporary tarsorrhaphy, the tarsorrhaphy can be expected to last a maximum of six weeks. Due to the very thin sutures used to tie the lids together, the sutures have a tendency to pull through or "cheesewire" through the thin tissue of the eyelids. It would be of great advantage if a temporary tarsorrhaphy could be performed which would prevent "cheesewiring", as well as allowing the entire eye to be viewed and allow the eyelids to be easily opened and reclosed without having to reperform the tarsorrhaphy.

SUMMARY OF THE INVENTION

One object of the present invention is a method for performing a temporary tarsorrhaphy wherein a first tube is inserted in a linear fashion through a portion of the upper eyelid of an eye so that a portion of the first tube lies beneath the skin of the eyelid and each end of the first tube protrudes from the upper eyelid. A second tube having first and second ends is inserted through a portion of the lower eyelid of the eye in a linear fashion so that each end of the second tube also protrudes from the lower eyelid. The protruding ends of the first and second tubes preferably lie approximately parallel to the eyelid margin. The first ends of the first and second tubes are drawn and secured together in a reversible manner. The second ends of the first and second tubes are also drawn and secured together in a reversible manner to complete a temporary tarsorrhaphy.

Another object of the present invention is a device comprising a tarsorrhaphy clip further comprising a tube having first and second ends and a connecting means having first and second ends. A clip may be attached to each eyelid of an eye, and the clips are secured together in a reversible manner with one or more fasteners. To attach the first clip to the upper eyelid, a first tube is inserted in a linear fashion through a portion of the upper eyelid of an eye so that a portion of the tube lies beneath the skin of the eyelid, and each end of the tube protrudes from the upper eyelid. Preferably, the end portions of the tube that lie outside the skin of the eyelid are parallel to the palpebral fissure. A first connecting means is then placed between the two protruding ends of the first tube, and a portion of the first tube located proximate the first end of the tube is attached to the first end of the first connecting means. The first tube is then drawn taut, and the second end of the first connecting means tube is attached to a portion of the tube proximate the second end of the first tube, such that the connecting means secures portions of the first tube which protrude from the eyelid, completing placement of the first clip. Once secured in place, the first clip lies approximately parallel to the palpebral fissure.

A similar procedure is used to attached the second clip to the lower eyelid of the eye. A second tube having first and second ends is inserted through a portion of the lower eyelid of the eye in a linear fashion so that each end of the second tube also protrudes from the lower eyelid. A portion of the second tube proximate to the first end of the tube is attached to the first end of a second connecting means. The second tube is then drawn taut, and a portion of the second tube proximate the second end of the tube is firmly secured to the second end of the second connecting means. The second clip is positioned on the eyelid approximately parallel to the palpebral fissure.

In a preferred embodiment, the connecting means each comprise a metal rod, each have a cylindrical sleeve covering the mid portion of each rod to protect the eyelid from abrasion. Additionally, in the preferred embodiment, each end of each connecting means comprises a small jawed clamp which can be locked down to hold a portion of a tube. In the preferred embodiment, after the ends of each tube have been secured by the connecting means, a small cap is placed over the ends of each jawed clamp to lock the clamp closed, if the jawed clamps are not self-locking.

After the first and second clips are attached to the eyelids, the eye is then closed so that the first connecting means on the upper eyelid and the second connecting means on the lower eyelid lie approximately parallel in close proximity to each other across the palpebral fissure. The first ends of each connecting means situated distal to the nose are bound together with one or more removable fasteners, preferably elastic bands. The second ends of each connecting means located proximate to the nose are then secured together in a similar manner. The fasteners can be removed at any time so that the eye may be opened and the condition of the eye assessed by the ophthalmic practitioner. The eye may be resealed by reattaching the fasteners to the ends of the connecting means in the manner previously described.

It is also an object of the present invention to provide a method for using a tarsorrhaphy device. Initially, an injection of a local anesthetic such as 1–2% lidocaine is injected into the upper eyelid using a hypodermic needle. The site of the injection should be located approximately where the center of a tarsorrhaphy clip will be after it has been attached to the eyelid. A raised blister on the upper eyelid results from the injection. The injection needle is then passed fully through the raised blister and made to exit through the skin at a point parallel to the eyelid margin approximately 5–10 mm from the entrance site, the distance being approximately equivalent to the length of the connecting means.

A hypodermic needle is used as the injecting needle which has an adequate internal diameter to accommodate the tube. The injecting needle is then used as a means to introduce the first tube under the skin along the eyelid margin. The first tube is inserted into one end of the injecting needle and fed into the needle until the first end of the tube which had been inserted into the needle projects from the tip of the needle. The protruding first end of the tube is held firmly and the needle removed from the blister, leaving the first tube inserted through the raised blister, with the first and second ends extending from each of the needles' exit and entrance sites, respectively. The first connecting means is then placed between the ends of the first tube and a portion of the tube proximate to its first end is attached to the first end of the first connecting means, preferably by means of a jawed clamp attached to the first end of the connecting means. If the jaws of the clamp are not self-locking, a cap may be placed over the ends of the jaws to hold the jaws firmly together. The tube is then drawn taut, and a portion of the tube proximate to the second end of the tube is then clamped firmly between the opposing locking jaws of the jawed clamp attached to the second end of the connecting means. A second cap may be placed over the ends of the jaws, if required. At this point, the first connecting means is secured in position along the margin of the upper eyelid. The first connecting means is approximately parallel to a palpebral fissure.

The identical procedure is then conducted on the lower eyelid, concluding with portions of the second tube of the lower eyelid being held securely in the jawed clamps attached to each end of the second connecting means. The eye is then closed, and the connecting means are then situated directly adjacent and approximately parallel to one another across the palpebral fissure. The first ends of the first and second connecting means are fastened together in a reversible manner, preferably with one or more elastic bands. Similarly, the second ends of the first and second connecting means are then fastened together in a reversible manner.

It is another object of the present invention to provide a method for performing a temporary tarsorrhaphy comprising inserting a first tube having first and second ends through a portion of the upper eyelid of an eye in a linear fashion so that a portion of the tube lies beneath the skin of the eyelid and the first and second ends of the tube protrudes from the eyelid. A second tube having first and second ends is inserted through a portion of the lower eyelid of the eye in a similar fashion so that the first and second ends of the second tube also protrude from the lower eyelid. The first ends of the first and second tubes are directly fastened together in a reversible manner. The second ends of the first and second tubes are then directly fastened together in a reversible manner to narrow the palpebral fissure and complete the temporary tarsorrhaphy.

Another object of the present invention is to provide a device for forming a temporary tarsorrhaphy comprising a first tube at least partially embedded in an upper eyelid, having a first end and a second end which protrude from the upper eyelid, and a second tube at least partially embedded in a lower eyelid having a first end and a second end which protrude from the lower eyelid. The first ends of the first and second tubes are drawn and fastened directly together via tying, heat fusing, or other reversible methods known in the art. The second ends of the first and second tubes are then drawn and fastened directly together in a reversible manner by the means previously described.

An additional object of the present invention is a method for performing a temporary tarsorrhaphy comprising implanting a first tube having first and second ends in an upper eyelid of an eye so that a portion of the tube lies beneath the skin of the eyelid, and having the first and second ends of the tube protruding from the upper eyelid. A second tube is then implanted in the lower eyelid of an eye so that a portion of the second tube is subcutaneous and the first and second ends of the second tube protrude from the lower eyelid. The first ends of the first and second tubes are drawn and secured together in a reversible manner with a clamping means. The second ends of the first and second tubes are then drawn and secured together in a reversible manner with a second clamping means to complete the temporary tarsorrhaphy.

A further object of the present invention is a device for performing a temporary tarsorrhaphy comprising a first tube having first and second ends which may be inserted through a portion of the upper eyelid of an eye so that a portion of the tube lies beneath the skin of the eyelid, having the first and second ends of the tube protruding from the upper eyelid. The device also comprises a second tube having first and second ends which may be inserted through a portion of the lower eyelid of the eye such that the first and second ends of the second tube also protrudes from the lower eyelid. Optionally, each tube may be hollow and include a means for stiffening each tube such as a wire, needle, or similar material which may be inserted through the tube to add rigidity and/or strength to the tube. A first clamping means for drawing and securing together in a reversible manner the first ends of the first and second tube is attached proximate to the first ends of the first and second tubes. A second clamping means for drawing and securing together in a reversible manner the second ends of the first and second tubes is then attached to the second ends of the tubes. The clamping means are preferably jawed clamps.

An additional object of the present invention is a method for performing a temporary tarsorrhaphy comprising implanting a first tube having first and second ends in an upper eyelid so that a portion of the tube lies beneath the skin of the eyelid and the first and second ends of the first tube protrude from the upper eyelid. A second tube having first and second ends is then inserted through a portion of the lower eyelid of an eye so that a portion of the tube lies beneath the skin of the eyelid and the first and second ends protrude from the upper eyelid. The first ends of the first and second tubes are fastened directly together in a reversible fashion. The second ends of the first and second tubes are then drawn and secured together in a reversible manner with a clamping means to complete the temporary tarsorrhaphy.

Still another object of the present invention is a device for performing a temporary tarsorrhaphy comprising a first tube having first and second ends which may be inserted in a linear fashion through a portion of the upper eyelid of an eye so that a portion of the tube lies beneath the skin of the eyelid and the first and second ends protrude from the upper eyelid. The device further comprises a second tube which may be inserted through a portion of the lower eyelid of the eye such that the first and second ends of the second tube also protrude from the lower eyelid. The first ends of the first and second tubes are fastened directly together in a reversible fashion. A clamping means for drawing and securing together the second ends of the first and second tubes in a reversible manner is then attached to the second ends of the tubes.

Further objects, features and advantages of the invention will be apparent from the following detailed non-limiting description when taken in conjunction with the accompanying drawings.

BRIEF DESCRIPTION OF THE DRAWINGS

In the drawings:

FIG. 1 is a front view of a closed eye having a first tube inserted through a raised blister on the upper eyelid.

FIG. 2 is a top view of a connecting means in accordance with the present invention.

DETAILED DESCRIPTION OF THE INVENTION

Figure 3:
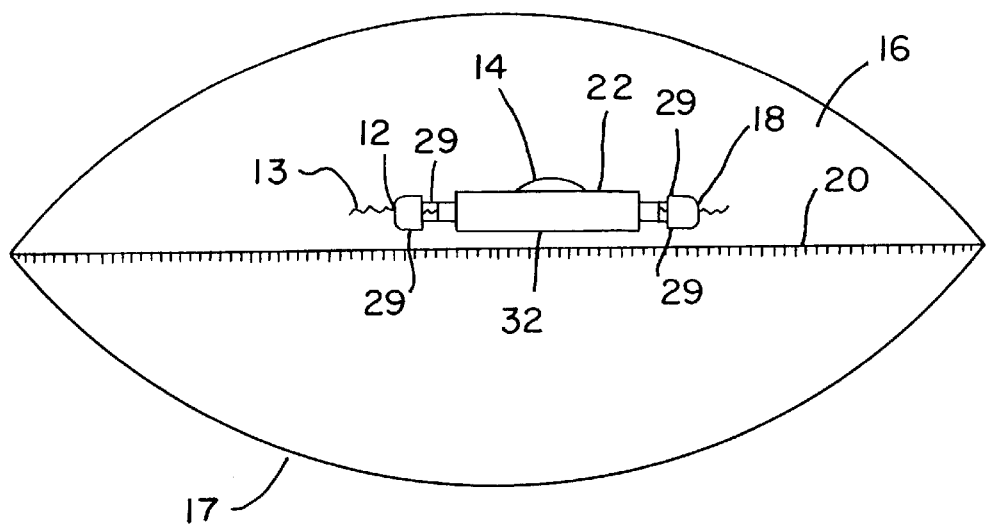
FIG. 3 is a front view of an eye illustrating a mounted tarsorrhaphy clip in accordance with the present invention.

In accordance with the present invention, one embodiment of a tarsorrhaphy device is a pair of clips each comprising a tube which is surgically implanted in a linear fashion in an eyelid such that the tube has a subcutaneous center portion and end portions which protrude from the eyelid. Portions of the protruding ends of each tube are fastened together with a connecting means having first and second ends. The temporary tarsorrhaphies are performed by mounting a tarsorrhaphy clip on each of the upper and lower eyelids of an eye and securing the first ends of the first and second connecting means together by means of one or more fasteners. The second ends of the first and second connecting means are secured together in a similar fashion to complete the temporary tarsorrhaphy. The connecting means are secured together in a reversible manner using such fasteners as elastic bands, wires, or other connecting materials which may be easily removed and replaced in order to allow the eye to be opened at will and inspected by the ophthalmic practitioner.

A tarsorrhaphy clip comprises a tube and a connecting means. Any tube utilized for performing a temporary tarsorrhaphy according to the present invention consists of a section of metal, plastic, rubber, silicone, wire, suture thread or similar material, any of which may optionally be sheathed by a nonabrasive coating, or other similar biocompatible materials known in the art that are durable and exhibit a high tensile strength while maintaining a very narrow diameter. The preferred material is silicone. The diameter of the tubing should be less than 300 microns, preferably 100–200 microns, and have a length of approximately 10–20 mm.

A first tarsorrhaphy clip is mounted on the upper eyelid of an eye as follows. The first end 13 of a first tube 12 is passed through a raised portion 14 of the upper eyelid 16 of eye 17 such that approximately 5 to 10 mm of the tube 12 is beneath the surface of the upper eyelid, as shown in FIG. 1. The first tube 12 is now positioned so that the central 5 to 10 mm of the tube 12 lies beneath the surface of the upper eyelid 16 and the first end 13 and second end 18 of the tube 12 are roughly parallel to the eyelid margin 20.

A first connecting means 22 as illustrated in FIG. 2 is then used to secure portions of the tube 12 proximate to the first and second ends. A connecting means comprises a rod to which the ends of the tubes may be secured. In preferred embodiments, each end of the connecting means will have a holding means attached thereto consisting of jawed clamps, wires, spring clips or other similar holding means known in the art. The connecting means 22 comprises a rod 24 having a first end 25 and a second end 26. The rod 24 consists of plastic, stainless steel, or other biocompatible material. The preferred material is stainless steel. The rod 24 has a preferred thickness of 25 to 22 gauge, and is approximately 5–10 mm in length. At each end of the rod 24 is a holding element 28. As illustrated, each holding element 28 consists of an opposable set of jawed members 29 which may be brought together in an interlocking fashion to secure a portion of a tube. Alternative holding elements may consist of pressure clamps, or any other means known in the art for firmly securing wires, tubes or similar materials. The jawed members 29 may be self-locking, or may be held closed by any method commonly known in the art, for example, caps, wires or spring clips. The preferred material for closing the jawed members which are not self-locking is a cap. As shown in FIG. 2, the jawed members 29 are secured with caps 30. Caps 30 comprise rubber, plastic or other suitable materials which may be slid or screwed over the closed jawed members 29 in order to securely close and lock the members 29, as well as protect the eyelid from being injured by the tips of the jawed members 29.

The connecting means 22 may optionally be partially ensconced in a cylindrical sleeve 32 which covers the central portion of the connecting means 22, as illustrated in FIG. 2. The sleeve 32 comprises a soft cushion of foam, rubber, plastic or other similar material which helps protect the eyelid from abrasion by the connecting means 22. The preferred materials are foam and rubber. The caliber of the connecting means with cushion sheath 32 is preferably 20 or 18 gauge.

As shown in FIG. 3, a portion of tube 12 proximate to first end 13 is attached to the connecting means 22 by enclosing it between the jawed members 29 attached to the first end 25 of connecting means 22. The term "proximate" is herein defined as any portion of the tube which lies between the point at which the tube exits the eyelid and the end of the tube. The jawed members 29 are closed to firmly grasp a portion of tube 12. Cap 30 is then placed over the ends of the jawed members 29 to prevent the members from opening. Tube 12 is pulled taut, and jawed members 29 attached to second end 26 of the connecting means 22 are clamped to a portion of the tube 12 proximate the second end 18 of the tube 12. Cap 30 is placed over jawed members 29 attached to second end 26 in the manner previously described to secure the first connecting means 22 to the upper eyelid 16.

Figure 4:
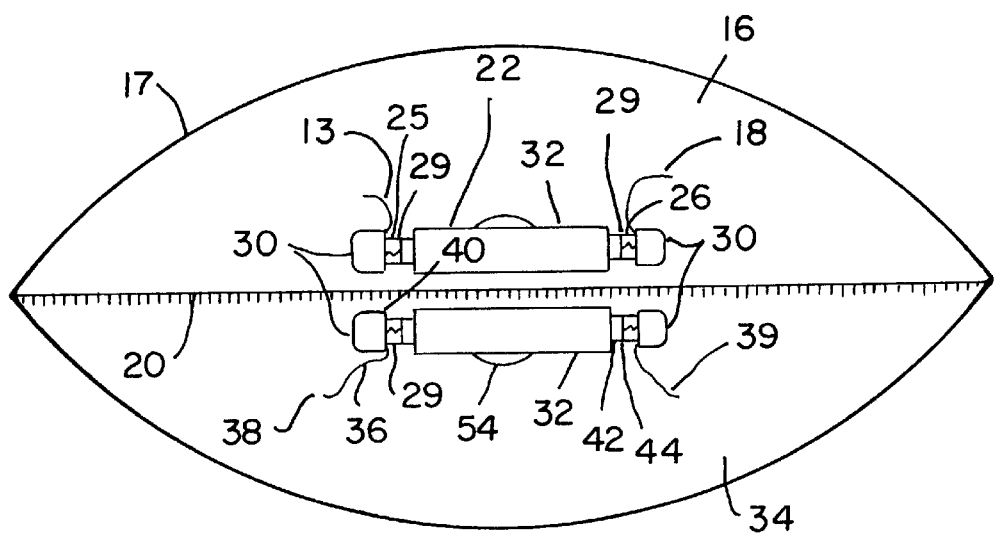
FIG. 4 is a front view of an eyelid having two tarsorrhaphy clips mounted parallel to each other.

As shown in FIG. 4, the procedure is repeated using lower eyelid 34, with a second tube 36 having a first end 38 and a second end 39 being partially implanted under the lower eyelid 34 such that a portion of the tube 36, preferably 5–10 mm, is subcutaneous. After implantation, tube 36 lies approximately parallel to the eyelid margin 20. A portion of the second tube 36 proximate the first end 38 is firmly clasped between the jawed members 29 attached to a first end 40 of a second connecting means 42. The jawed members 29 are locked closed with the cap 30. Second tube 36 is drawn taut. A portion of tube 36 proximate the second end 39 is firmly secured between the jawed members 29 at the second end 44 of the second connecting means 42, and the cap 30 placed over the jaws 29 as previously described.

Figure 5:
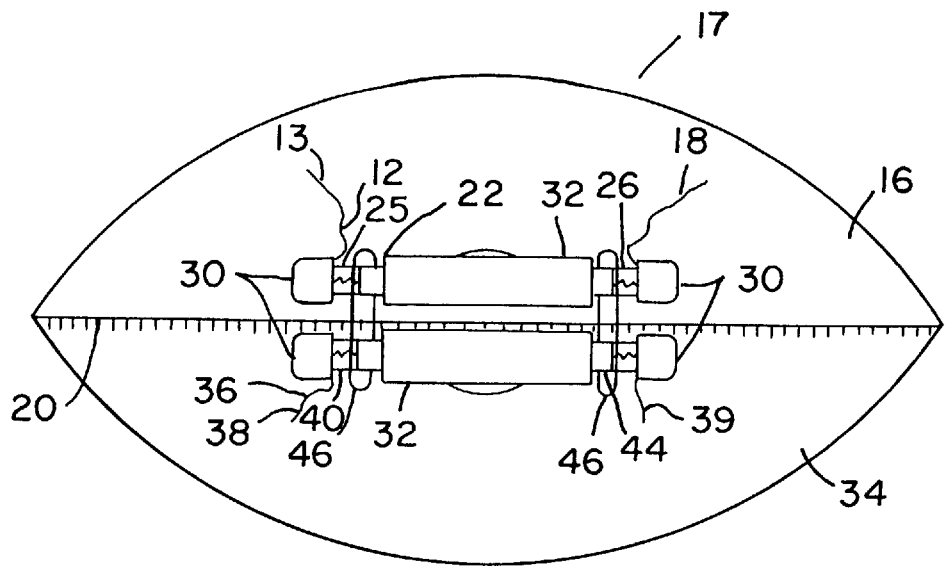
FIG. 5 is a front view illustrating a temporary tarsorrhaphy completed in accordance with the present invention.

The eye is then closed, allowing the connecting means 22 and 42 to lie roughly parallel to each other across the palpebral fissure. The first ends 25 and 40 of the connecting means 22 and 42, respectively, are secured together in a reversible fashion using one or more fasteners 46, as shown in FIG. 5. Such fasteners may consist of clamps, elastic bands, wires, or other suitable materials known in the art. The preferred fastener is a small elastic band such as rubber bands used in orthodontia. One or more fasteners 46 are then used to secure the second ends 26 and 44 of the connecting means 22 and 42, respectively, together in a reversible fashion. Alternatively, the connecting means 22 and 42 may be held together by placing one or more fasteners around the center portion or other parts of both connecting means. The fasteners 46 may be removed periodically so that the eye 17 may be opened and inspected. After inspection of the eye 17, the fasteners 46 are then reattached.

The method of the present invention comprises the insertion of a first tube through a portion of the upper eyelid of an eye so that a portion of the tube lies beneath the skin of the upper eyelid and each end of the first tube protrudes from the upper eyelid. A second tube having first and second ends is then inserted through a portion of the lower eyelid of the eye so that a portion of the second tube is subcutaneous while allowing each end of the second tube to protrude from the lower eyelid. The first ends of the first and second tubes are drawn and secured together in a reversible manner. The second ends of the first and second tubes are then drawn and secured in a reversible manner. Drawing and securing the tubes together may be accomplished by directly fastening the first ends and the second ends of the tubes together respectively, or by use of connecting means or clamping means described herein or any feasible combination thereof.

Figure 6:
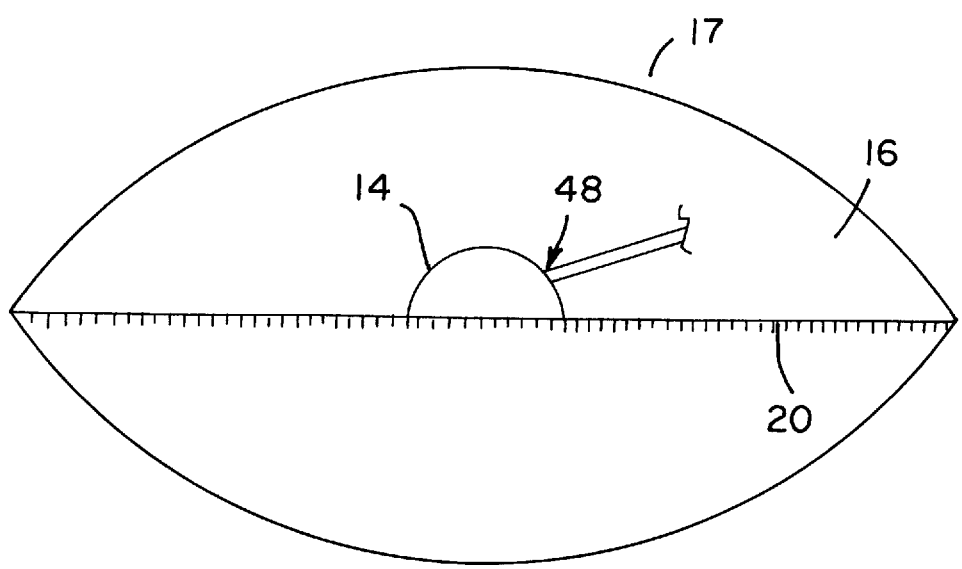
FIG. 6 is a front view of a raised blister being formed on an upper eyelid by subcutaneous injection of an anesthetic.

An illustration of a method of the present invention is as follows. As shown in FIG. 6, the tip of a hypodermic needle 48 is inserted beneath the skin of the upper eyelid 16. An anesthetic, preferably 1 or 2% lidocaine, is injected beneath the eyelid skin near eyelid margin 20, to raise a blister 14 beneath the skin. The hypodermic needle 48 has an appropriate internal diameter so as to adequately accommodate the diameter of the tubes 12 and 36.

Figure 7:
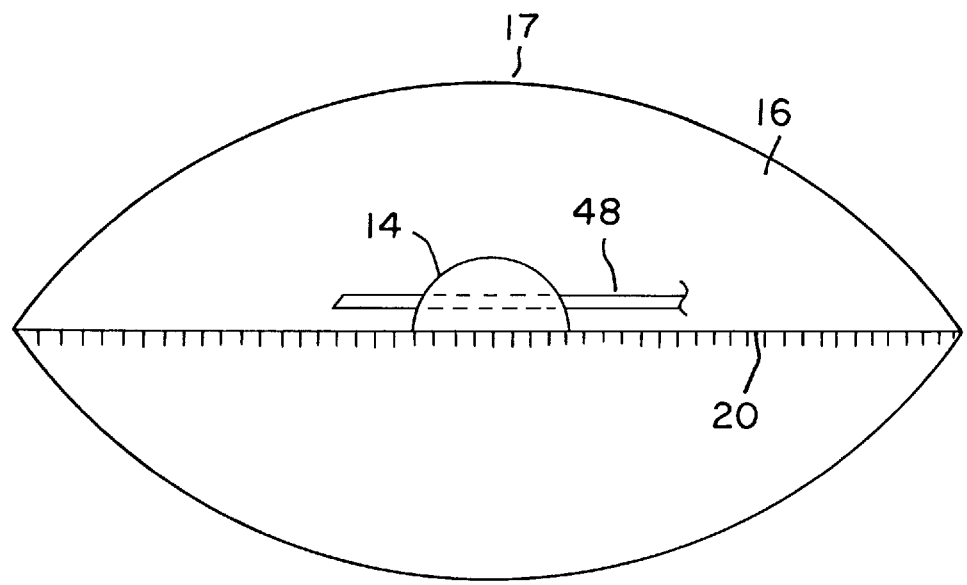
FIG. 7 is a front view of an injecting needle passed through a raised blister on an upper eyelid parallel to the eyelid margin.

The hypodermic needle 48 is then passed into the blister 14 which has been created by the local anesthetic and directed parallel to the eyelid margin 20. The needle 48 is then made to exit through the blistered skin at a point along the eyelid margin approximately 5–10 mm from the entrance site as shown in FIG. 7. This distance will be approximately the same as the length of the connecting means 22 and 42.

Figure 8:
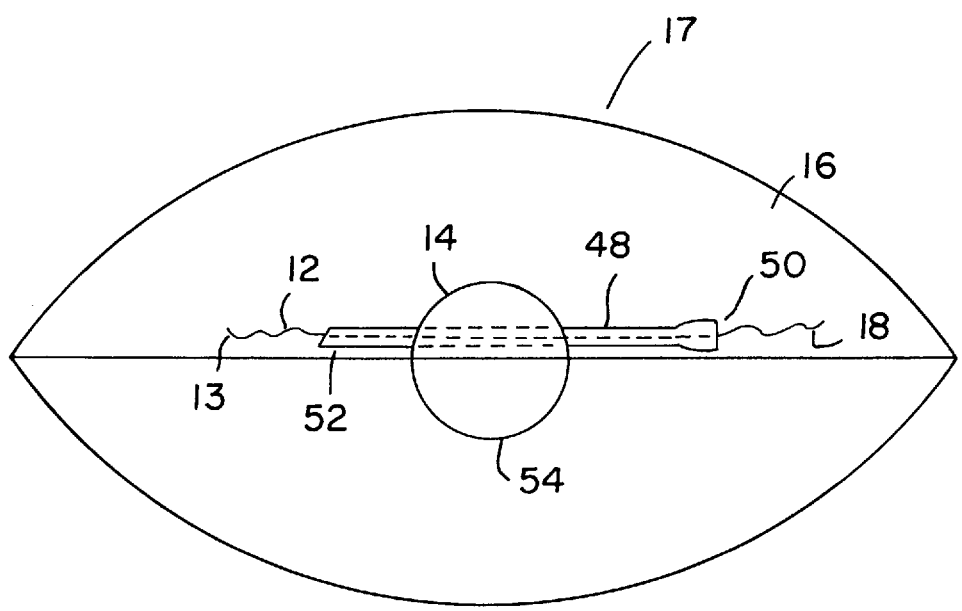
FIG. 8 is a front view of a tube being passed through a hypodermic needle that has been inserted through a raised blister on the upper eyelid.

The hypodermic needle 48 is then used to introduce the first tube 12 into place. The tube 12 is inserted into the first end 50 of hypodermic needle 48, and threaded through hypodermic needle 48 until it emerges from tip 52 as shown in FIG. 8. The hypodermic needle 48 is then carefully removed, leaving tube 12 in place, such that approximately 5–10 mm of the tube 12 is subcutaneous. As shown in FIG. 8, the ends 13 and 18 of the tube 12 protrude from each side of the raised blister 14.

The first connecting means 22 is then placed between the ends of the first tube 12. The jawed members 29 located at first end 25 of connecting means 22 are then closed around a portion of the first tube 12 proximate to the first end 13. The cap 30 is placed over the jawed members 29 to firmly close and lock the jawed members 29 at first end 25 to firmly hold a portion of the tube 12. The tube 12 is pulled taut, and the jawed members 29 attached to the second end 26 of the connecting means 22 are closed around a portion of the tube 12 proximate to the second end 18. The cap 30 is placed over the end of the jawed members 29 to securely close and lock the jawed members 29. The steps are then repeated with the lower eyelid 34. Hypodermic needle 48 is used to create a second blister 54 on the lower eyelid 34, and the second tube 36 is threaded through the second blister 54 in the manner previously described, as shown in FIG. 8. A portion of the second tube 36 proximate the first end 38 is firmly clasped between the jawed members 29 attached to first end 40 of the second connecting means 42. The jawed members 29 are locked closed with the cap 30, as shown in FIG. 4. The second tube 36 is drawn taut, and a portion of the tube 36 proximate the second end 39 is firmly secured between the jawed members 29 located at the second end 44 of the second connecting means 42. The cap 30 is placed over the jawed members 29 as previously described.

The connecting means 22 and 42 are then in position along the margin 20 of each of the upper and lower eyelids when the eye 17 is closed, as shown in FIG. 4. The connecting means are directly adjacent and roughly parallel to one another across the eyelid margin 20. Finally, one or more fasteners 46 preferably consisting of one or more elastic bands are used to secure the first ends 25 and 40 of the connecting means 22 and 42, respectively, together in a reversible fashion as shown in FIG. 5. Identical fasteners 46 are used to secure second ends 26 and 44 together in a reversible manner. The fasteners 46 may be easily removed when required so that the eye may be inspected. Alternatively, one or more fasteners 46 may be placed about the center portion of the first and second connecting means 22 and 42, respectively, to secure the connecting means together. This allows easy, safe and convenient periodical inspection of the eye to be accomplished, without requiring additional surgery each time the temporary tarsorrhaphy needs to be undone.

Figure 9:
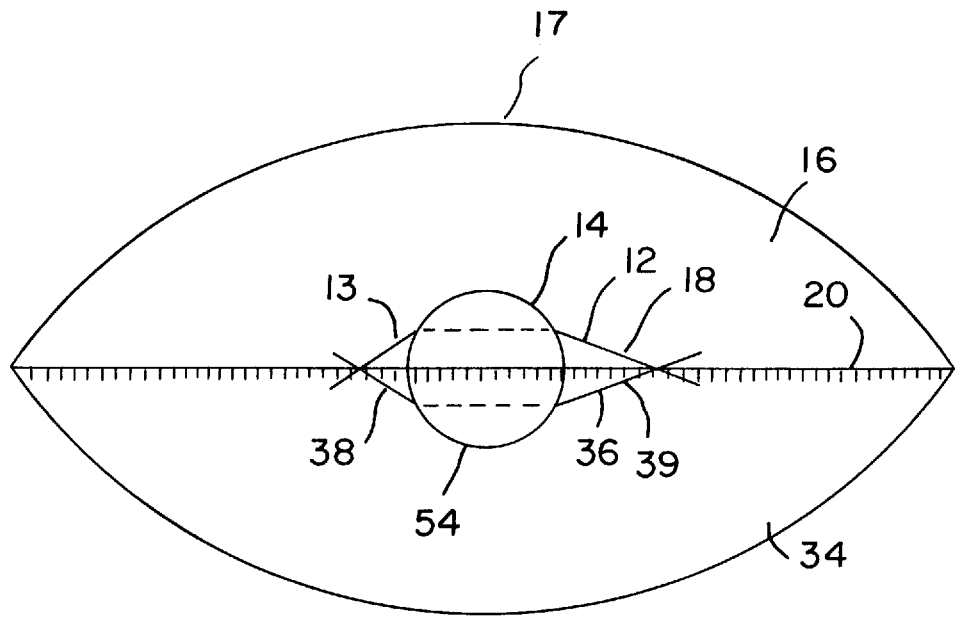
FIG. 9 is a front view illustrating an alternative embodiment of a temporary tarsorrhaphy completed in accordance with the present invention.

In an alternative embodiment of the present invention, tube 12 and tube 36, respectively, are implanted in the upper 16 and lower 34 eyelids of an eye in the manner previously described. The first ends 13 and 38 of the tubes 12 and 36, respectively, are directly fastened together in a reversible manner as shown in FIG. 9. The fastening may consist of tying the tubes together directly or interlinking the tube ends or heat sealing the tube ends together, or any other similar means for fastening which allow the first ends and second ends of the tubes to be attached in a reversible manner so that the physician may inspect the eye as required. In a similar fashion, the second ends 18 and 39 of the first and second tubes 12 and 36, respectively, are fastened together in a similar manner to complete the temporary tarsorrhaphy. Note that although the first ends of the tubes are both illustrated as lying adjacent to each other, the first ends of the tubes may lie opposite one another, in this and the following alternative embodiments.

Figure 10:
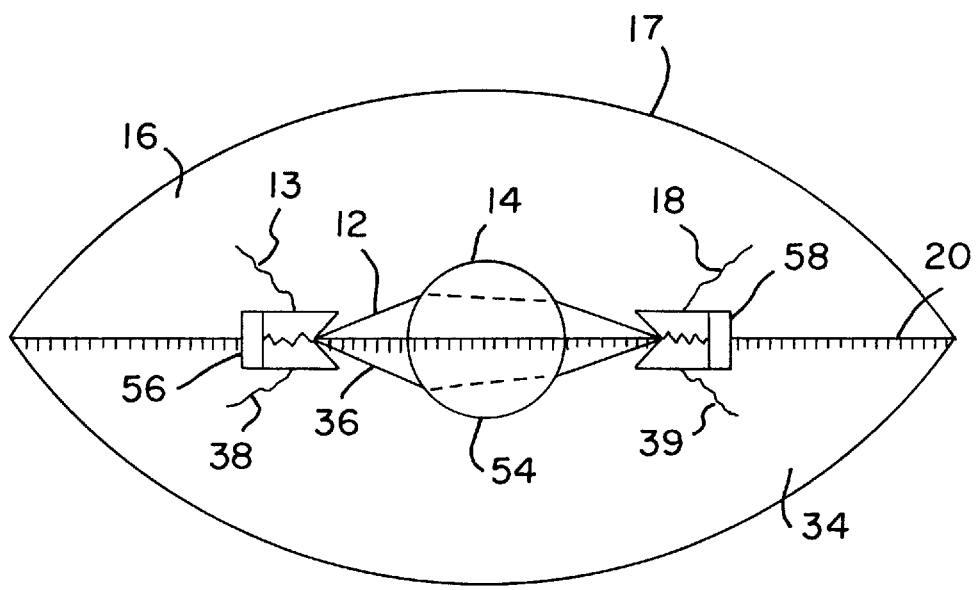
FIG. 10 is a front view illustrating a second alternative embodiment of a temporary tarsorrhaphy completed in accordance with the present invention.
Figure 11:
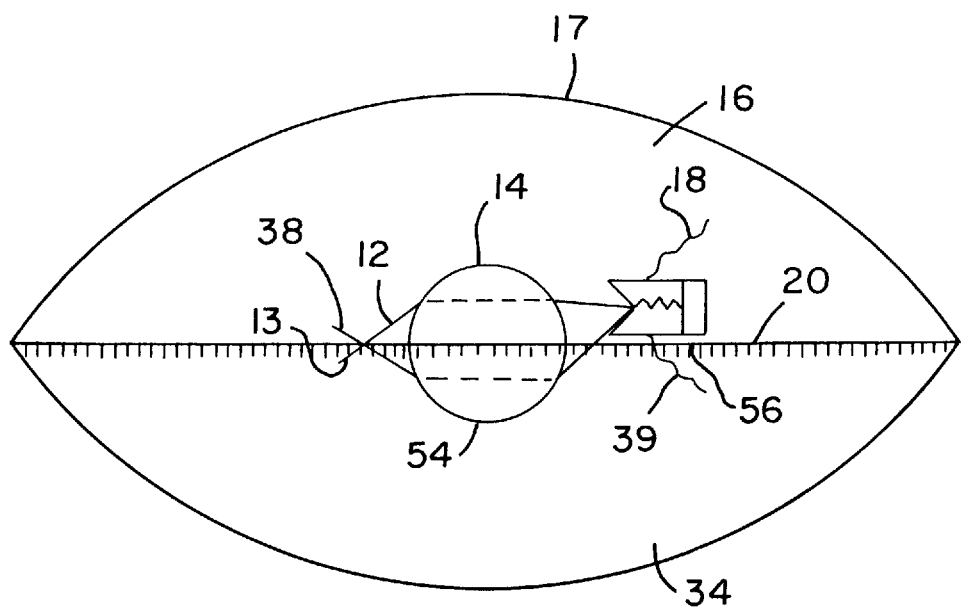
FIG. 11 is a front view illustrating a third alternative embodiment of a temporary tarsorrhaphy completed in accordance with the present invention.

In another alternative embodiment, as shown in FIG. 10, the first ends 13 and 38 of the first and second tubes 12 and 36, respectively, may be drawn and held together by first clamping means 56. Second ends 18 and 39 of the first and second tubes may be drawn and held together by a second clamping means 58. Clamping means 56 and 58 may comprise jawed clamps, as illustrated, or may comprise spring clamps, wire, or other means known or used in the art which may be used to firmly draw and hold together the first ends of the first and second tubes. Alternatively, clamping means 56 and 58 may be similar to the connecting means 22 and 42 previously described, comprising a rod with first and second ends and a holding element at each end.

In another alternative embodiment, the tubes 12 and 36 are implanted in the eye 17 in the manner previously described. The first ends 13 and 38 of the first and second tubes 12 and 36, respectively, may be directly fastened together in a reversible manner by tying, interlinking or heat fusing the tube ends together, or other similar methods. The second ends 18 and 39 of the first and second tubes may be drawn and held together by a clamping means or connecting means, as previously described.

It is understood that the invention is not confined to the particular embodiments set forth herein as illustrative, but embraces all such forms thereof as come within the scope of the following claims.

What is claimed is:

1. An assembly for performing a temporary tarsorrhaphy comprising:
   (a) a first tube which may be at least partially embedded in an upper eyelid, having a first end and a second end;
   (b) a second tube which may be at least partially embedded in a lower eyelid, having a first end and a second end;
   (c) a first connecting means for drawing and securing together portions of the first tube proximate the first and second ends;
   (d) a second connecting means for drawing and securing together portions of the second tube proximate the first and second ends; and
   (e) one or more fasteners securing the first and second connecting means together in a reversible manner.

2. The assembly of claim 1 wherein each of the first and second tubes is comprised of a material selected from the group consisting of plastic, rubber, silicone, suture thread and metal.

3. The assembly of claim 1 wherein each of the first and second connecting means is comprised of stainless steel.

4. The assembly of claim 1 wherein each of the first and second connecting means further comprises a first and second end, each end having a set of jawed members attached thereto.

5. The assembly of claim 1, wherein each of the first and second connecting means further comprises a sleeve which covers at least a portion of the connecting means.

6. The assembly of claim 1, wherein the fasteners are elastic bands.

7. An assembly performing a temporary tarsorrhaphy comprising:
   (a) a first tube which may be at least partially embedded in an upper eyelid, having a first end and a second end;
   (b) a second tube which may be at least partially embedded in a lower eyelid, having a first end and a second end;
   (c) a first clamping means for drawing and securing together portions of the first tube and the second tube proximate the first end of each tube; and
   (d) a second clamping means for drawing and securing together portions of the first tube and the second tube proximate the second end of each tube.

8. The assembly of claim 7 wherein each of the first and second tubes is comprised of a material selected from the group consisting of plastic, rubber, silicone, suture thread and metal.

9. The assembly of claim 7 wherein each of the first and second clamping means is comprised of a clamp selected from the group consisting of spring clamps and jawed clamps.

10. The assembly of claim 7 wherein each of the first and second clamping means are jawed clamps.

11. The assembly of claim 10, wherein each of the first and second clamping means further comprises a protective sleeve which covers at least a portion of the clamping means.

12. An assembly for performing a temporary tarsorrhaphy comprising:
   (a) a rod having a first end and a second end;
   (b) a first set of jawed members attached to the first end of the rod;
   (c) a second set of jawed members attached to the second end of the rod; and (d) a protective sleeve covering a portion of the rod.

13. An assembly for performing a temporary tarsorrhaphy comprising:
   (a) a first tube having a first end and a second end, such that a portion of the first tube may be embedded in an upper eyelid with the first and second ends protruding from the upper eyelid;
   (b) a second tube having a first end and a second end, such that a portion of the second tube may be embedded in a lower eyelid with the first and second ends protruding from the lower eyelid;
   (c) a first connecting means for drawing and securing together portions of the first tube proximate the first and second ends of the first tube, comprising a first rod having a first end and a second end, having a portion of the first rod covered by a first sleeve, and having a first set of jawed members attached to the first end of the first rod, and a second set of jawed members attached to the second end of the first rod, the first end of jawed members securing a portion of the first tube proximate the first end of said tube, and the second set of jawed members securing a portion of the first tube proximate the second end of said tube;
   (d) a second connecting means for drawing and securing together portions of the second tube proximate the first and second ends of the second tube, comprising a second rod having a first end and a second end, having a portion of the second rod covered by a second sleeve, and having a first set of jawed members attached to the first end of the second rod, and a second set of jawed members attached to the second end of the second rod, the first set of jawed members securing a portion of the second tube proximate the first end of said tube, and the second set of jawed members securing a portion of the second tube proximate the second end of said tube; and
   (e) one or more fasteners joining in a reversible manner the first connecting means to the second connecting means.

14. An assembly for performing a temporary tarsorrhaphy comprising:
   (a) a first tube having first and second ends, the first tube having size and shape to be at least partially embedded in an upper eyelid having first and second ends, the second tube having size and shape to be:
   (b) a second tube at least partially embedded in an upper eyelid, having a first end and a second end; wherein the first ends of the first and second tubes are drawn and fastened directly together in a reversible manner and the second ends of the first and second tubes are drawn and fastened directly together in a reversible manner.

15. The assembly of claim 14 wherein the first and second tubes are comprised of materials selected from the group consisting of plastic, rubber, silicone, suture thread and metal.

16. A method for performing a temporary tarsorrhaphy, comprising:
   (a) inserting through a portion of an upper eyelid a first tube having a first end and a second end such that the ends of the tube protrude from the upper eyelid;
   (b) inserting through a portion of a lower eyelid a second tube having a first end and a second end such that the ends of the tube protrude from the lower eyelid;
   (c) drawing and securing together portions of the first tube proximate the first and second ends of said tube with a first connecting means comprising a rod and having first and second ends;
   (d) drawing and securing together portions of the second tube proximate the first and second ends of said tube with a second connecting means comprising a rod having first and second ends; and
   (e) securing the first and second connecting means together with one or more fasteners, to complete the temporary tarsorrhaphy.

17. The method of claim 14, steps (a) and (b) further comprising the steps of:
   (i) injecting a local anesthetic subcutaneously into the upper eyelid to produce a first raised blister of skin;
   (ii) passing a hypodermic needle completely through the first blister such that there is both an entrance and exit site of the needle in the first blister;
   (iii) feeding the first tube completely through the needle such that an end of the tube protrudes from each end of the needle;
   (iv) removing the needle from the first blister, leaving the first tube in place such that a portion of the first tube remains beneath the skin of the upper eyelid and each end of the tube protruding from the upper eyelid;
   (v) injecting the local anesthetic subcutaneously into the lower eyelid to produce a second raised blister of skin;
   (vi) passing the hypodermic needle completely through the second blister such that there is both an entrance and exit site of the needle in the second blister;
   (vii) feeding the second tube completely through the needle such that an end of the tube protrudes from each end of the needle; and
   (viii) removing the needle from the second blister, leaving the second tube in place such that a portion of the second tube remains beneath the skin of the lower eyelid and each end of the second tube protruding from the lower eyelid.

18. A method for performing a temporary tarsorrhaphy comprising:
   (a) inserting through a portion of an upper eyelid a first tube having first and second ends such that the ends of the tube protrude from the upper eyelid;
   (b) inserting through a portion of a lower eyelid a second tube having first and second ends such that the ends of the tube protrude from the lower eyelid;
   (c) drawing and directly fastening together the first ends of the first and second tubes in a reversible manner; and
   (d) drawing and directly fastening together the second ends of the first and second tubes in a reversible manner to narrow the palpebral fissure in order to complete the temporary tarsorrhaphy.

19. A method for performing a temporary tarsorrhaphy comprising:
   (a) inserting through a portion of an upper eyelid a first tube having first and second ends such that the ends of the first tube protrude from the upper eyelid;
   (b) inserting through a portion of a lower eyelid a second tube having first and second ends such that the ends of the second tube protrude from the lower eyelid;
   (c) drawing and securing together the first ends of the first tube and the second tube in a reversible manner with a first clamping means; and
   (d) drawing and securing together the second ends of the first tube and the second tube in a reversible manner with a second clamping means to narrow the palpebral fissure and complete the temporary tarsorrhaphy.

20. A method for performing a temporary tarsorrhaphy comprising:
- (a) inserting through a portion of an upper eyelid a first tube having first and second ends such that the ends of the first tube protrude from the upper eyelid;
- (b) inserting through a portion of a lower eyelid a second tube having first and second ends such that the ends of the second tube protrude from the lower eyelid;
- (c) drawing and securing together the first ends of the first tube and the second tube in a reversible manner with a first clamping means; and
- (d) drawing and directly fastening together the second ends of the first and second tubes in a reversible manner to narrow the palpebral fissure in order to complete the temporary tarsorrhaphy.

* * * * *